United States Patent [19]

Saisho

[11] Patent Number: 4,940,697
[45] Date of Patent: Jul. 10, 1990

[54] INJECTION MATERIAL FOR COSMETIC TREATMENT

[76] Inventor: Atsushi Saisho, 3-9-10, Miyamaedaira, Miyamae-ku, Kawasaki-shi, Kanagawa, Japan

[21] Appl. No.: 204,188

[22] Filed: Jun. 8, 1988

[30] Foreign Application Priority Data

Dec. 4, 1987 [JP] Japan ................... 62-305812

[51] Int. Cl.$^5$ ........................................ A61K 31/695
[52] U.S. Cl. ........................................ 514/63; 128/21; 514/770
[58] Field of Search .................. 514/63, 770; 128/21

[56] References Cited

PUBLICATIONS

Chemical Abstract, 1982, Kao Soap, vol. 97, p. 203098p.
Maekawa et al., 1984, vol. 108, No. 3, Abstract of Journal of Cancer Research & Clinical Oncology article, pp. 364–365.
Tanaka, et alk, 1985, vol. 25, No. 9, Abstract of Clinical Neurology, pp. 1075–1080.

*Primary Examiner*—Dale R. Ore
*Attorney, Agent, or Firm*—Flynn, Thiel, Boutell & Tanis

[57] ABSTRACT

Disclosed is a material for an injection used in cosmetic treatment, which comprises, as the base oil, dimethylpolysiloxane represented by the following formula:

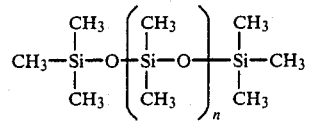

and, incorporated therein as the filler, hydrophobic silica represented by the following formula:

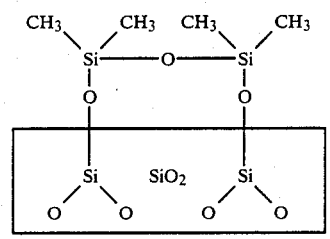

This material satisfies all of the conditions requisite for an injection material for cosmetic treatment, and when this material is hypodermically injected, neither system disorder nor local disorder such as flare, swelling or formation of tumors occurs.

1 Claim, No Drawings

INJECTION MATERIAL FOR COSMETIC TREATMENT

BACKGROUND OF THE INVENTION (1) Field of the Invention

The present invention relates to a material for an injection used in cosmetic treatment such as rhinoplasty or plastic surgery on the temple, jaw, cheek or the like for cosmetic purposes.

(2) Description of the Related Art

As the material for an injection used in cosmetic treatment such as rhinoplasty, buildup of the temple, jaw, cheek or the like or lifting of wrinkles on the forehead, crow-feet wrinkles or other wrinkles, there have been heretofore used paraffin, Organogen (trade name) formed by mixing paraffin and vaseline with beeswax, Vioplax (trade name) formed by pressing a mixture of glycerol oleate, glycerol linoleate, glycerol palmitate and beeswax, Soft Ericon (trade name) formed by heat-pressing a mixture of a silicone oil with a crosslinking agent and a product synthesized by using dimethylpolysiloxane as the base oil and hydrophilic silica (supplied under a trade name "Aerosil 200" by DEGUSSA, West Germany) as the filler, which was previously developed by the present inventor.

Clinical conditions to be satisfied by a material to be hypodermically injected into the human body for cosmetic treatment are as follows:

(1) the material should be stable in a hot or cold condition, (2) it should not cause semipermanent injury when incorporated into the human body, (3) it should not cause any change in its nature when incorporated into the human body, (4) it should be readily disinfected, (5) it should be easily processable, (6) it can be extracted from the body according to need, (7) it should be non-absorptive, (8) it should be stable against mechanical shocks, (9) it should not be carcinogenic,

(10) it should not be causative of an allergic reaction,

(11) it should not be chemically active,

(12) it should not be hydrophilic but hydrophobic (it is not wetted with water and does not absorb water),

(13) it should neither be deformed in the body nor flow nor infiltrate into the organ, and

(14) it should cause neither inflammation nor foreign body reaction.

Injection materials customarily used for cosmetic treatment fail to satisfy all of the above-mentioned conditions completely, so that they often cause various troubles in the living body.

SUMMARY OF THE INVENTION

It is therefore a primary object of the present invention to provide a material for an injection used in cosmetic treatment, which satisfies all of the above-mentioned conditions completely.

More specifically, in accordance with the present invention, there is provided a material for an injection used in cosmetic treatment, which comprises, as the base oil, dimethylpolysiloxane represented by the following formula:

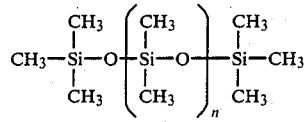

and, incorporated therein as the filler, hydrophobic silica represented by the following formula:

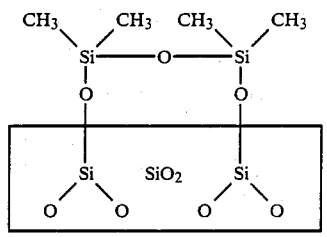

DETAILED DESCRIPTION OF THE PREFERRED EMBODIMENTS

It is preferred that the hydrophobic silica be incorporated in an amount of 20% to 30% by weight.

Amounts of approximately 20% by weight is effective for treatments of temple and wrinkles and amounts of approximately 30% by weight is desirable for rhinoplasty, plastic surgery on jaw, wrinkles, etc.

A product marketed under the trade name of "Aerosil R 972", which is manufactured by DEGUSSA, West Germany, and sold in Japan by Nippon Aerosil Kabushiki Kaisha, is used as the hydrophobic silica and incorporated in the above-mentioned dimethylpolysiloxane.

In the production of "Aerosil R 972" (silica not containing adsorbed water), dimethyldichlorosilane and water vapor are introduced with an appropriate inert gas, such as nitrogen, into a fluid bed type reactor heated at about 400° C. In the reactor, chemical reaction occurs between silanol group on the surface of silica and dimethyldichlorosilane and hydrochloride liberated from the reaction is removed.

In the successive procedure, the resulting product is taken out of the reactor. In the product thus obtained, the chlorine content is not more than 0.05% and siloxane bond which is formed due to the high reaction temperature may be partially remained on the surface of particles of the product.

When the above material was injected and the observation was continued for one year, no clinical disorder was found and no damage was checked in the pathological and histological test.

The present invention will now be described in detail with reference to the following Example.

EXAMPLE

A purified medicinal dimethylpolysiloxane having a viscosity of 12,500 cSt and represented by the following formula:

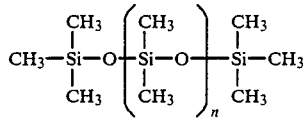

was mixed with about 20% by weight of hydrophobic silica represented by the following formula as the filler:

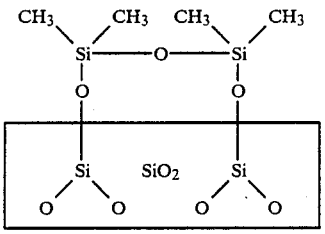

and the mixture was kneaded with vigorous stirring to obtain an injection material. As the hydrophobic silica, "Aerosil R972" previously mentioned was used.

In the animal experiment, 2 cc each of the obtained injection material was hypodermically injected into neck portions, waist portions and back portions of several cats two years old or older, and after the lapse of 10 days, 2 months, 3 months and one year, the injected material and surrounding tissues were extracted and subjected to the pathological and histological test at the Research and Development Center of Hygienic Science, Kitazato University, located at Shirogane, Minato-ku, Tokyo, Japan. No malignant image was observed at all.

The above injection material was hypodermically injected to 400 subjects for clinical administration since 1983, and the state was observed with the lapse of time. Neither systemic disorder nor local disorder such as flare, swelling or formation of tumors was observed in any of the subjects.

As is apparent from the foregoing description, the present invention provides an injection material for cosmetic treatment such as rhinoplasty or plastic surgery on the temple, jaw, cheek or the like for cosmetic purposes, which satisfies all of the clinical conditions requisite for a material to be hypodermically injected, and this material does not cause any of clinical disorders, such as a local disorder, for example, flare, swelling or formation of tumors or the like, and a systemic disorder.

What is claimed is:

1. A hypodermically injectable composition for cosmetic plastic surgery, which consists essentially of a mixture of (1) dimethylopolysiloxane oil suitable for subcutaneous hypodermic injection into the patient's body, said oil having a viscosity of 12,500 cSt and having the following formula:

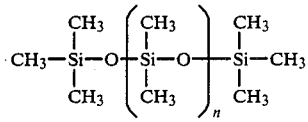

and, (2) from 20 to 30 percent by weight of hydrophobic silica filler having the following formula:

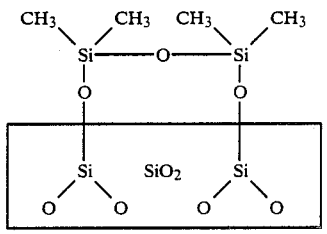

said filler having been prepared by reacting dimethyldichlorosilane with the silanol groups on the surface of silica, at about 400° C., and removing the hydrogen chloride that is formed by the reaction.

* * * * *